(12) United States Patent
O'Shaughnessy et al.

(10) Patent No.: US 7,903,706 B2
(45) Date of Patent: Mar. 8, 2011

(54) COMPACT, THERMALLY STABLE MULTI-LASER ENGINE

(76) Inventors: John O'Shaughnessy, Carlsbad, CA (US); David E. Hargis, San Diego, CA (US); Steven Lee Miller, Golden, CO (US); Mark Lin, Carlsbad, CA (US)

( * ) Notice: Subject to any disclaimer, the term of this patent is extended or adjusted under 35 U.S.C. 154(b) by 39 days.

(21) Appl. No.: 12/418,537

(22) Filed: Apr. 3, 2009

(65) Prior Publication Data

US 2009/0274176 A1    Nov. 5, 2009

Related U.S. Application Data

(60) Provisional application No. 61/042,652, filed on Apr. 4, 2008.

(51) Int. Cl.
| | |
|---|---|
| *H01S 3/04* | (2006.01) |
| *H01S 3/10* | (2006.01) |
| *H01S 5/00* | (2006.01) |
| *G01N 21/01* | (2006.01) |
| *G01N 1/10* | (2006.01) |

(52) U.S. Cl. .................. 372/34; 372/22; 372/23; 372/36; 372/50.121; 356/244; 356/246

(58) Field of Classification Search .............. 372/22–23, 372/34–36, 38.01; 356/244, 246
See application file for complete search history.

(56) References Cited

U.S. PATENT DOCUMENTS

| | | | |
|---|---|---|---|
| 5,544,271 A | 8/1996 | Lim | |
| 6,048,444 A * | 4/2000 | Takahashi et al. | 204/603 |
| 6,101,201 A | 8/2000 | Hargis et al. | |
| 6,133,995 A * | 10/2000 | Kubota | 356/73 |
| 6,215,807 B1 * | 4/2001 | Reilly | 372/57 |
| 6,221,671 B1 * | 4/2001 | Groner et al. | 436/63 |
| 6,480,513 B1 | 11/2002 | Kapany et al. | |
| 6,490,309 B1 * | 12/2002 | Okazaki et al. | 372/75 |
| 6,592,822 B1 * | 7/2003 | Chandler | 422/82.05 |
| 6,603,780 B2 * | 8/2003 | Miyai | 372/23 |
| 6,920,159 B2 | 7/2005 | Sidorin et al. | |
| 6,980,293 B1 * | 12/2005 | Harada | 356/317 |
| 7,505,495 B2 * | 3/2009 | Fratti et al. | 372/34 |
| 7,548,567 B2 | 6/2009 | Kupershmidt et al. | |
| 2001/0017868 A1 * | 8/2001 | Kraenert et al. | 372/23 |
| 2001/0021210 A1 | 9/2001 | Nakaya et al. | |
| 2002/0097772 A1 | 7/2002 | Dautremont-Smith et al. | |
| 2004/0027631 A1 * | 2/2004 | Nagano et al. | 359/196 |
| 2004/0210289 A1 | 10/2004 | Wang et al. | |
| 2005/0220458 A1 | 10/2005 | Kupershmidt et al. | |
| 2005/0281298 A1 | 12/2005 | Kupershmidt et al. | |
| 2006/0239317 A1 * | 10/2006 | Yoshida et al. | 372/36 |
| 2006/0273260 A1 * | 12/2006 | Casstevens et al. | 250/458.1 |
| 2009/0257054 A1 | 10/2009 | Hargis et al. | |

* cited by examiner

*Primary Examiner* — Minsun Harvey
*Assistant Examiner* — Phillip Nguyen
(74) *Attorney, Agent, or Firm* — Knobbe, Martens, Olson & Bear, LLP

(57) ABSTRACT

Various embodiments of a multi-laser system are disclosed. In some embodiments, the multi-laser system includes a plurality of lasers, a plurality of laser beams, a beam positioning system, beam focusing optics, a thermally stable enclosure and a temperature controller. The thermally stable enclosure is configured to thermally and mechanically couple to a flow cell. The thermally stable enclosure substantially comprises a material with high thermal conductivity. The thermally stable enclosure can have a relatively small volume.

33 Claims, 3 Drawing Sheets

COMPACT, THERMALLY STABLE MULTI-LASER ENGINE

RELATED APPLICATIONS

This application claims the benefit of U.S. Provisional Application No. 61/042,652, filed Apr. 4, 2008, which is incorporated herein by reference in its entirety.

BACKGROUND

1. Field

This disclosure generally relates to optical (e.g. fluorescent, spectroscopic) analysis of flow cells, and to, for example, compact, thermally stable multi-laser systems configured to couple to flow cells and to provide illumination thereto.

2. Description of Related Art

Optical analysis of flow cells, such as laser-induced fluorescence, involves illuminating biological samples with laser light in order to test samples which may, for example, be tagged with fluorescent dyes. Fluorescent dyes absorb light at certain wavelengths and in turn emit their fluorescence energy at a different wavelength. This emission can be detected to ascertain properties of the fluid in the flow cell. Existing systems for fluorescent analysis of flow cells, however, suffer from various drawbacks, such as measurement error.

SUMMARY

Embodiments described herein have several features, no single one of which is solely responsible for their desirable attributes. Without limiting the scope of the invention as expressed by the claims, some of the advantageous features will now be discussed briefly.

Various embodiments described herein provide the ability to perform optical measurements on flow cells while addressing some of the drawbacks encountered with conventional approaches, such as laser beam alignment to the flow cell that is sensitive to the ambient temperature resulting in signal power fluctuations.

A wide range of embodiments are disclosed. Some embodiments, for example, comprise a compact, thermally stable multi-laser system. The multi-laser system comprises a plurality of lasers. The plurality of lasers outputs a plurality of respective laser beams. The system further comprises a beam positioning system. The beam positioning system is configured to position the plurality of laser beams closer together. The multi-laser system further comprises beam focusing optics. The beam focusing optics are configured to focus the plurality of laser beams. The multi-laser system further comprises a thermally stable enclosure. The thermally stable enclosure encloses the plurality of lasers, the beam positioning system and the beam focusing optics. The thermally stable enclosure is configured to thermally and mechanically couple to a flow cell. The thermally stable enclosure substantially comprises a material with high thermal conductivity of at least 5 W/(m K). The thermally stable enclosure has a volume of no more than 36 cubic inches. The system further comprises a temperature controller. The temperature controller is configured to control the temperature of the thermally stable enclosure and to maintain the alignment of the focused laser beams to the flow cell over a range of ambient temperatures. Other embodiments are also disclosed.

BRIEF DESCRIPTION OF THE DRAWINGS

The following drawings and the associated descriptions are provided to illustrate embodiments of the present disclosure and do not limit the scope of the claims.

DETAILED DESCRIPTION OF PREFERRED EMBODIMENTS

Although certain preferred embodiments and examples are disclosed herein, inventive subject matter extends beyond the specifically disclosed embodiments to other alternative embodiments and/or uses of the inventions, and to modifications and equivalents thereof. Thus, the scope of the inventions herein disclosed is not limited by any of the particular embodiments described below. For example, in any method or process disclosed herein, the acts or operations of the method or process may be performed in any suitable sequence and are not necessarily limited to any particular disclosed sequence.

For purposes of contrasting various embodiments with the prior art, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

In order to perform testing of biological samples, flow cells are illuminated with laser beams. Fluorescent dyes absorb light at certain wavelengths and in turn emit their fluorescence energy at a different wavelength. This emission can be detected to ascertain properties of the fluid in the flow cell. Temperature variations may cause the wavelength and/or the intensity of light output by the lasers to vary. Such variations in the laser beams directed into the flow cell may cause fluctuations in output fluorescent signals, which may introduce inaccuracy in the optical measurements. Temperature variations and/or temperature gradients also may cause movement of the optical elements and resultant shifting of the laser beams. These pointing errors may cause the laser beams to deviate from the flow cell, such that the signal changes, or is altogether lost, again introducing inaccuracy in the test results.

Temperature variations can result from ambient temperature fluctuations. Accordingly, reducing the temperature variation of and the presence of temperature gradients within the laser beam system can improve the accuracy and usability of the test results.

Figure 1:
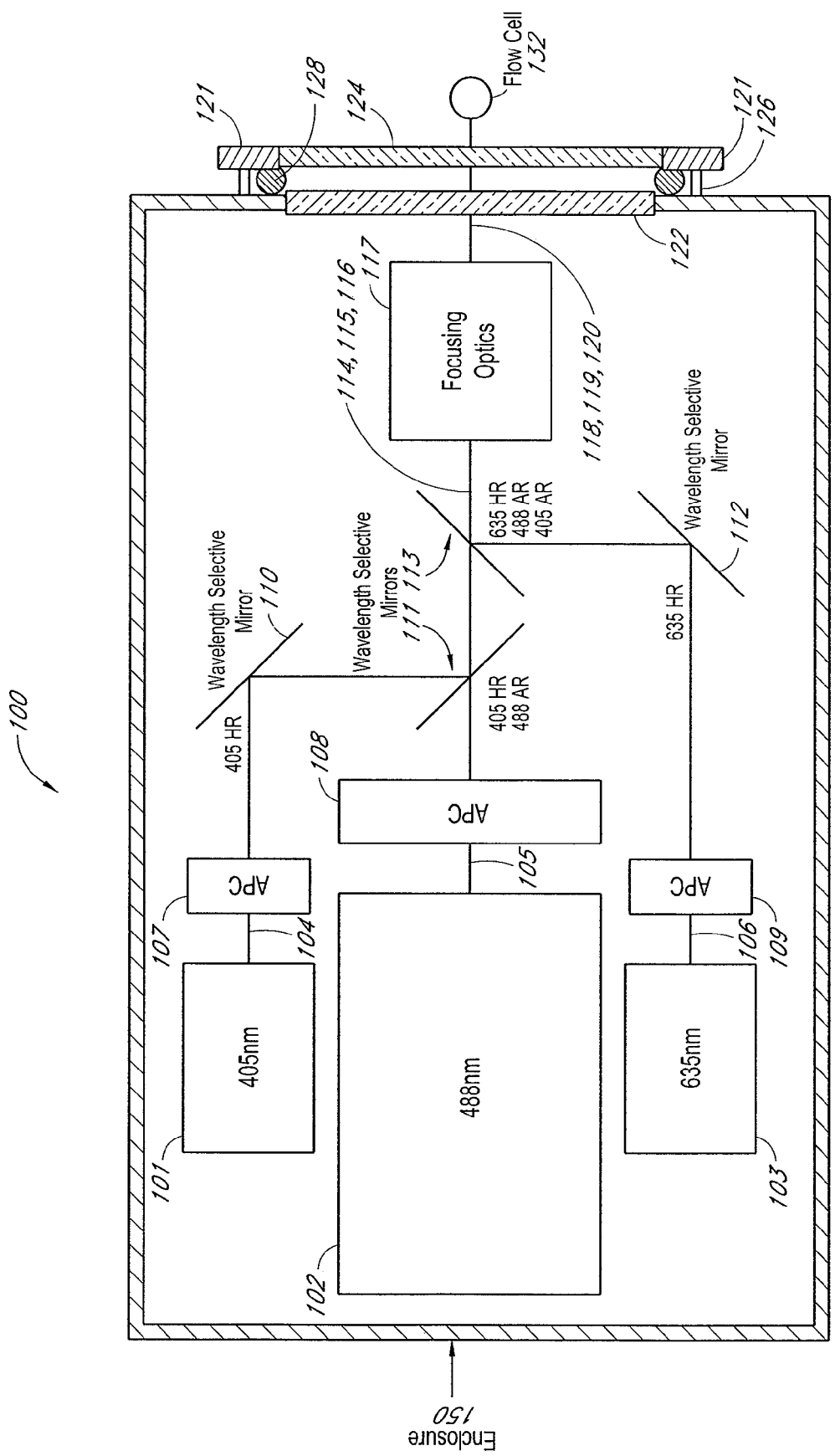
FIG. 1 depicts a multi-laser system for performing optical measurements on flow cells.

Various embodiments described herein may address one or more of these problems. FIG. 1 is a top view of a multi-laser system 100. The multi-laser system 100 depicted comprises a thermally stable enclosure 150 configured to mechanically and/or thermally couple to a flow cell 132. The thermally stable enclosure 150 helps to isolate the laser and optics within the enclosure 150 from the ambient environment, which may have varying temperature. In some embodiments, the enclosure 150 can achieve thermal stability through the use of a temperature controller, as discussed in relation to FIG. 2 below. In various embodiments, the enclosure 150 helps reduce variations in the temperature of the various components of the multi-laser system 100. By maintaining the temperature within the enclosure within a relatively small range, thermally induced laser wavelength and intensity fluctuations as well as pointing instabilities of the laser beams can be reduced or minimized. Accordingly, the use of a thermally stable enclosure 150 may help achieve more accurate test results.

In some embodiments, the temperature across the enclosure may be stable over time and with changes in the ambient temperature. The constant temperature over time may help with long term system performance. For example if the enclosure temperature were to change with time, then the system performance would also potentially degrade with time. This could eventually result in servicing the system, e.g., to realign the system.

The thermally stable enclosure 150 comprises a material with high thermal conductivity. In some embodiments, a material with thermal conductivity of at least about 5 W/(m K), (e.g., between about 5 W/(m K) and about 2000 W/(m K)) is used. In some embodiments, a material with thermal conductivity at least about 50 W/(m K) (e.g. between about 50 W/(m K) and about 2000 W/(m K)) is used. In other embodiments, a material with thermal conductivity of about 375 W/(m K) or greater is used. In other embodiments, a material with thermal conductivity of at least about 380 W/(m K) is used. The use of such thermally conductive material helps ensure a relatively reduced temperature variation within the enclosure 150, even when the ambient temperature outside of the enclosure varies relatively widely.

Some materials expand and contract when heated or cooled. Changes in the enclosure temperature or temperature variations across the enclosure can result in a change in the relative positions of lasers, mirrors, lenses and flow cell. Some lasers exhibit beam pointing that is temperature dependent. This may be due in part to the fact that different materials are used in the construction of the laser, (metals, glass, adhesives etc). The different materials may have different thermal expansion coefficients which may cause beam deviations when the laser's temperature is changed. Some mirror and lens systems also show some temperature dependence for the same reason.

As described more fully below, a temperature controller in thermal contact with the enclosure adjusts the temperature of the enclosure in response to variations in ambient conditions. A highly thermally conductive enclosure enables the temperature controller to more quickly and effectively maintain the enclosure and system temperature without temperature gradients in response to such variations in ambient conditions. A variety of thermally conductive materials can be used (e.g. copper, aluminum, copper tungsten, ceramics, epoxy, etc.). In some embodiments, a material with a thermal conductivity of at least 5 W/(m K) may be used. In other embodiments, a material with a thermal conductivity of less than 5 W/(m K) may be used. The thermally conductive material can be used to form the entire enclosure, or merely a portion thereof. In certain embodiments, the enclosure substantially comprises highly thermally conductive material. For example, highly thermally conductive material can be used to form the top, the bottom, or any number of the sides of the enclosure 150, or any combination thereof. In some embodiments, a majority of the enclosure 150 is made of the substantially thermally conductive material. In some embodiments, only a relatively small portion of the enclosure 150 is made of the thermally conductive material. In some embodiments, a substantial portion of the enclosure 150 is made of the substantially thermally conductive material. In some embodiments, multiple substantially thermally conductive materials can be used, with some areas of the enclosure 150 being more thermally conductive than others.

The multi-laser system 100 includes a plurality of lasers 101, 102 and 103 enclosed within the thermally stable enclosure 150. Although FIG. 1 includes three lasers, a different number of lasers can be used. The plurality of lasers 101, 102, 103 may comprise of diode lasers, solid-state lasers, frequency-doubled lasers or other types of lasers that produce light useful in optical (e.g. fluorescent, spectroscopic) analysis. The multi-laser system 100 shown in FIG. 1 includes a 405nm laser, a 488nm laser and a 635nm laser, but other common wavelengths of laser can be used (e.g. lasers having wavelengths of 375nm, 440nm, 515nm, 561nm, 594nm, 640nm).

The plurality of lasers 101, 102, 103 output a plurality of respective laser beams 104, 105 and 106. Laser beam 104 has a first wavelength, laser beam 105 has a second wavelength, and laser beam 106 has a third wavelength. The first, second and third wavelengths are different from one another. In FIG. 1, these wavelengths are 405nm, 488nm and 635nm respectively, but other common wavelengths can be used (e.g. 375nm, 440nm, 515nm, 561nm, 594nm, 640nm).

As shown in FIG. 1, the multi-laser system 100 further includes a plurality of automatic power control (APC) modules 107, 108 and 109. In some embodiments, the APC modules 107, 108 and 109 may each comprise a beamsplitter (not shown) and a photodetector (not shown) configured to sample light from the laser beams 104, 105 and 106 respectively, and to feedback the signal from the detector in communication with a laser controller (not shown) to adjust the output power of lasers 101, 102 and 103 respectively. Other approaches may be possible.

Referring still to FIG. 1, the multi-laser system 100 further includes a beam positioning system comprising a plurality of wavelength selective mirrors 110, 111, 112 and 113. In various embodiments, the wavelength selective mirrors have significantly different reflection or transmission properties at different wavelengths. Accordingly, the wavelength selective mirrors can separate or combine laser beams with different wavelengths. Through the use of suitable optical coatings, wavelength selective mirrors exhibit high reflection over some range of wavelengths, and high transmission over another range of wavelengths. The wavelength selective mirrors are appropriate for the wavelengths of the laser sources. For example, various of the wavelength selective mirrors will selectively reflect (or transmit) light of one laser and not light of another laser. FIG. 1 depicts four wavelength selective mirrors. In other embodiments, a different number of wavelength selective mirrors may be used. In some embodiments, the wavelength selective mirrors may comprise dichroic and trichroic mirrors. Dichroic mirrors can separate or combine lasers with two different wavelengths. Trichroic mirrors can separate or combine lasers with three different wavelengths. Trichroic mirrors may be optimized for three wavelengths; they may have three peaks or one broad peak that covers multiple wavelengths. In other embodiments, the wavelength selective mirrors may comprise mirrors with selectivity for a different number of wavelengths. Alternatively, substantially non-wavelength selective mirrors that do not selectively reflect (or transmit) light of one laser and not light of another laser may be inserted in the path of the beam to redirect and/or alter the beam path or the beam. Similarly other optical elements can be inserted into the optical path.

The wavelength selective mirrors 110, 111, 112, and 113 are configured with highly reflective and anti-reflective coatings in accordance with the wavelengths of the plurality of laser beams 104, 105 and 106. As shown in FIG. 1, wavelength selective mirror 110 is configured to be highly reflective of the wavelength of the laser beam 104 (e.g. 405nm); wavelength selective mirror 111 is configured to be highly reflective of the wavelength of the laser beam 104 (e.g. 405nm) and anti-reflective of the wavelength of the laser beam 105 (e.g. 488nm); wavelength selective mirror 112 is configured to be highly reflective of the wavelength of the laser beam 106 (e.g. 635nm) and wavelength selective mirror 113 is configured to be highly reflective of the wavelength of the laser beam 106 (e.g. 635nm), and anti-reflective of the wavelengths of the laser beams 104 (e.g. 405nm) and 105 (e.g. 488nm). In other embodiments, the wavelength selective mirrors can be configured to be highly reflective of some wavelengths and anti-reflective of some other wavelengths in order to separate or combine the wavelengths as necessary.

In some embodiments, this plurality of wavelength selective mirrors 110, 111, 112 and 113 may be supported by a plurality of respective flexure mounts (not shown). Flexure mounts are less likely to move with external vibrations and thus are less likely to require adjustment. Flexure mounts reduce impact on the optics from shocks such as may be introduced by shipping of the system. Additionally, flexure mounts typically exhibit less hysteresis than rolling or sliding contacts. Flexure mounts are typically fabricated from materials which make them relatively less sensitive to temperature variations. Flexure mounts may also be smaller than conventional spring loaded mounts. In some embodiments, the flexure mounts may comprise a nickel-iron alloy material for example. Other materials may also be used. In other embodiments, the plurality of wavelength selective mirrors 110, 111, 112 and 113 may be supported by a plurality of respective spring-loaded mirror mounts (not shown).

In the multi-laser system 100 shown in FIG. 1, there are three optical paths depicted. A first optical path at a wavelength of 405 nm originates at laser 101, passes through the APC 107, where a portion of the signal is picked off (e.g. by a beam splitter), is then highly reflected at wavelength selective mirrors 110 and 111 and transmitted through wavelength selective mirror 113 and then arrives at the focusing optics 117. Similarly, a second optical path at a wavelength of 488nm originates at laser 102, passes through the APC 108, where a portion of the signal is picked off (e.g. by a beam splitter), is then transmitted through wavelength selective mirrors 111 and 113 and then arrives at the focusing optics 117. And, a third optical path at a wavelength of 635nm originates at laser 103, passes through the APC 109, where a portion of the signal is picked off (e.g. by a beam splitter), is then reflected at wavelength selective mirrors 112 and 113 and then arrives at the focusing optics 117. Propagating along these paths, laser beams 104, 105 and 106, which may have originally been far from one another, are repositioned to be closer together as beams 118, 119, 120. In some embodiments, the beams 118, 119 and 120 are parallel to one another. In other embodiments, the beams 118, 119 and 120 are not parallel to one another. Other mirrors and optical components (e.g. lenses, prisms, polarization rotators, waveplates, etc.) can be included to alter the laser beams and/or optical paths.

Still referring to FIG. 1, the multi-laser system 100 further includes beam focusing optics 117 to provide size reduction and/or shaping to the output laser beams 118, 119, 120. For example, the focusing optics 117 may focus a laser beam down to a smaller spot. Additionally, the focusing optics 117 may change the shape of the laser beams. In some embodiments, for example, the laser beams 118, 119 and 120 can have a generally Gaussian profile, so that when illuminating a flow cell, the intensity of the light illuminating the center of the flow cell is significantly greater than the intensity of the light illuminating the peripheral edges of the flow cell. Accordingly, the beams of light 118, 119, 120 can be elongated (e.g., elliptical) beams, so that the relatively high intensity center regions of the light beams extend across the entire width of the flow cell, while the relatively low intensity outer regions of the light beams do not strike the flow cell. By using an elongated (e.g., elliptical) beam of light, a more uniform distribution of light across the width of the flow cell can be achieved while illuminating a relatively small longitudinal area along the length of the flow cell and maintaining substantially uniform high light intensity.

In some embodiments, the beams 114, 115 and 116 enter the beam focusing optics 117 and can have circular cross-sections with a Gaussian fall-off. In some embodiments, the beam focusing optics 117 may include an anamorphic lens system which may produce non-rotationally symmetric or elongated beam such as a beam with elliptical cross-section and spot size. In other embodiments, the beam focusing optics 117 may include cylindrical lenses. In some embodiments, the beam focusing optics 117 may include spherical lenses. In some embodiment, the beam focusing optics 117 may include powell lenses (Gaussian to flat-top transformers). In some embodiments, the beam focusing optics 117 may include aspherical lenses. The focusing optics may be achromatic with reduced chromatic aberration thereby reducing positioning error which may otherwise result from different color laser beams. Accordingly, achromatic anamorphic optics, achromatic elliptical optics, achromatic spherical optics and achromatic aspherical optics, may be used. In some embodiments, lenses can be an anamorphic microlens array. In some embodiments, refractive and/or diffractive optics can be used to produce the elongated beams of light 118, 119, 120. Other types of optics are possible.

In cases where the laser comprises a semiconductor laser, the laser beam output may already be elliptical-shaped, and optics to convert the elliptical beam into a circular beam can be substantially excluded. In such cases, there would be no need to include anamorphic focusing optics to make the elliptical-shaped beam spherical (e.g. rotationally symmetric). Spherical or rotationally symmetric optics may be employed without anamorphic elements.

The output laser beams 118, 119 and 120 depicted in FIG. 1 may have respective spot sizes of between about 55 μm and 110 μm in one direction and between about 5 μm and 15 μm in the other direction. In other embodiments, the laser beams may have respective spot sizes of between about 70 μm and 110 μm in one direction and between about 5 μm and 15 μm in the other direction. In other embodiments, the laser beams may have spot sizes of between about 55 μm and 100 μm in one direction and between about 5 μm and 15 μm in the other direction. In other embodiments, the laser beams may have spot sizes of between about 70 μm and 100 μm in one direction and between about 5 μm and 15 μm in the other direction. These may correspond to major and minor axes of an ellipse for a beam with an elliptical cross-section and spot shape. In some embodiments, the output laser beams 118, 119 and 120 may have respective spot sizes of 80 μm in one direction and 10 μm in the other direction. In other embodiments, the output laser beams 118, 119 and 120 may have respective spot sizes of 100 μm in one direction and 10 μm in the other direction. Other sizes and shapes are possible for the light beams.

Still referring to FIG. 1, the multi-laser system 100 includes coupling to a flow cell 132. The multi-laser system 100 can include an output window 121 that allows the beams of light 118, 119 and 120 to exit the enclosure 150. The output window 121 can be made from, fused silica, glass or acrylic or a variety of other transparent materials (e.g. plastic). In some embodiments, the enclosure 150 includes an aperture 122 in a wall thereof and the output window 121 comprises a transparent window pane 124, positioned over the aperture 122. The window pane 124 can be made from, fused silica, glass or acrylic or a variety of other transparent materials (e.g. plastic). The aperture 122 and window pane 124 can assume a variety of shapes, but in some embodiments they are rectangular, circular or elliptical. The window 121 can be attached to the enclosure 150 by a plurality of fasteners such as bolts 126. In FIG. 1, only two bolts 126 are shown, but in some embodiments, additional bolts can be positioned along the edges of the window 121. In some embodiments, the window 121 can include a flange for mounting the window. The flange may have a plurality of through holes through which fasteners (e.g., bolts 126) can pass to secure the window 121 to the enclosure 150. A seal 128 (e.g., an O-ring) can be positioned between the enclosure 150 and the window 121. The bolts 126 can be tightened, causing the O-ring 128 to be compressed between the enclosure 150 and the window 121. In some embodiments, the O-ring 128 produces a hermetic seal. Other approaches can be used to fasten the window 121 to the enclosure 150. The window 121 can be secured to the enclosure 150 by an adhesive, epoxy, or cement.

In some embodiments, the seal described may produce a hermetic seal. A hermetic seal may help reduce particles and contamination from outside the enclosure. A hermetic seal may also help to prevent or reduce the flow of air currents and thus prevent or reduce the flow of ambient temperature changes into the enclosure. This in turn may help reduce temperature instability within the enclosure. In some of the embodiments discussed above, the entire enclosure 150 is hermetically sealed from the ambient air. Thus, the interior of the enclosure 150 is isolated from air currents which can cause temperature variation, and the internal optical elements are protected from external contaminants. In some embodiments a getter (not shown) is located inside the enclosure 150 which can reduce contaminant particles or chemical species. Additional, a desiccant (not shown) can be positioned inside the enclosure 150 to reduce moisture.

Although FIG. 1 shows a single output window, multiple output windows can be used. For example, each beam of light 118, 119, 120 can exit the enclosure 150 via a respective output window. In some embodiments, it is desirable that as much as possible of the enclosure 150 comprise the thermally conductive material, to better achieve temperature uniformity. Accordingly, the output windows can be separated by thermally conductive material and can cover only as much area as necessary to allow light beams 118, 119, 120 to leave the enclosure 150. However, in some embodiments a single output window is easier and less expensive to construct.

The multi-laser system 100 can include a flow cell connector (not shown) that is mechanically and thermally coupled to the enclosure 150, and the flow cell connector is configured to secure a flow cell 132 so that it intersects and maintains the alignment of the beams of light 118, 119, 120. In some embodiments, the flow cell connector can permanently attach the flow cell 132 to the enclosure 150. However, in some embodiments, the flow cell connector can allow the flow cell 132 to be removably attached to the enclosure 150. In some embodiments, the flow cell connector can be compatible with multiple types and/or sizes of flow cells. For example, the flow cell connector can include a clip, a friction or pressure fit coupling, a threaded portion configured to receive a corresponding threaded portion of the flow cell 132, or a variety of other connectors known in the art or yet to be devised. The flow cell 132 can be a capillary flow cell, and at least part of the flow cell can comprise a transparent material (e.g., fused silica or glass) that allows the light beams 118, 119, 120 to enter the flow cell 132 and interact with a sample fluid contained within the flow cell 132. The flow cell 132 can be a thin hollow tube, forming a flow path that has a diameter of about 10 μm. Other flow cell types and/or sizes can be used, and the flow cell 132 can be oriented differently than as shown in FIG. 1. In some embodiments, the beams of light 118, 119, 120 strike the flow cell over areas centered about 110 μm to 140 μm apart from each other, and in some embodiments, 125 μm apart from each other. In some embodiments, the thermally stable enclosure 150 matches the thermal expansion coefficient of the flow cell 132. Matching of thermal expansion coefficients may help reduce overall stress on the flow cell. For some forms of optical measurements, it may be desirable for the different laser beams to be focused to different locations in the flow cell 132 at specific locations (e.g., areas spaced about 125 μm apart).

Figure 2:
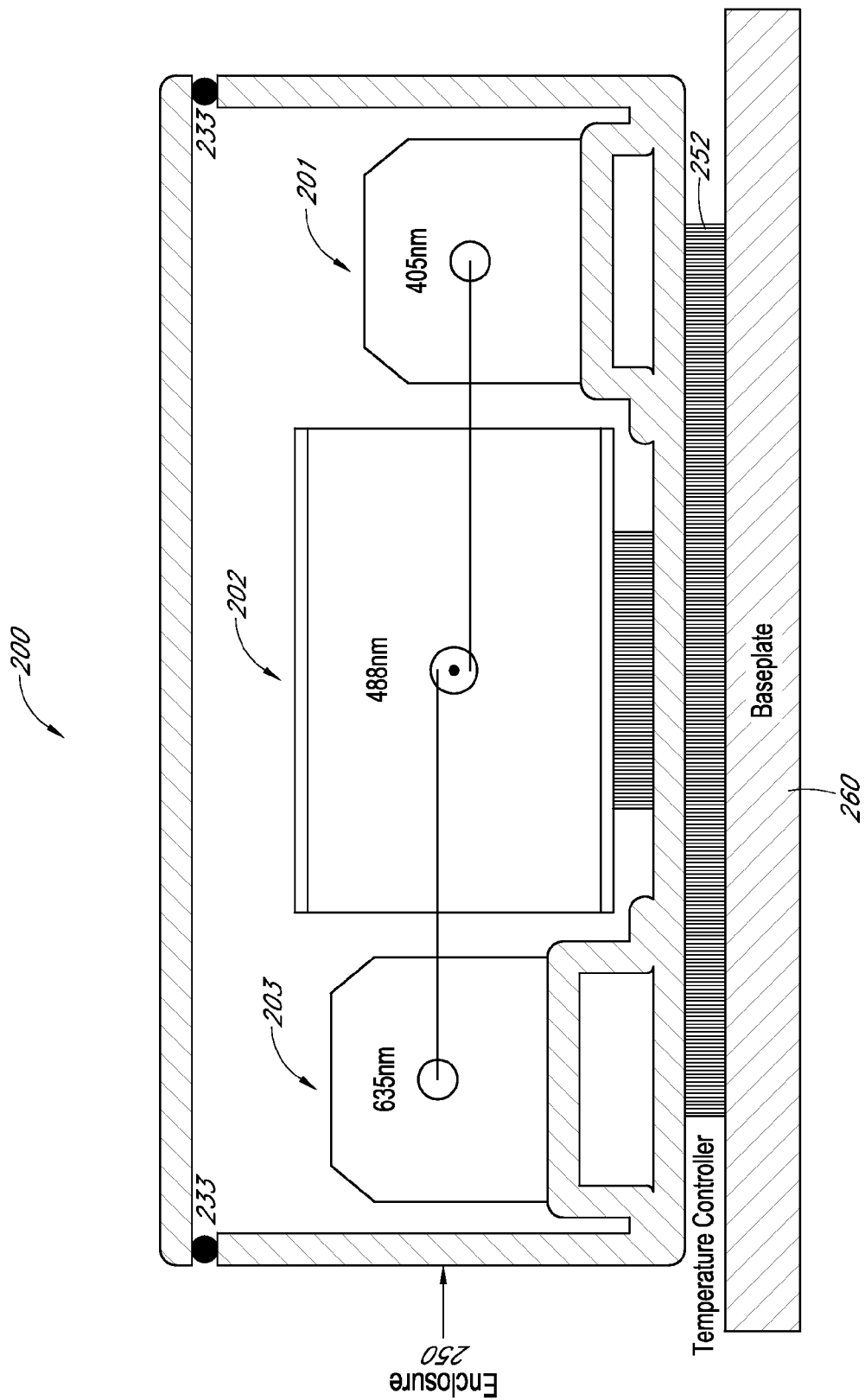
FIG. 2 depicts the front view of the system of FIG. 1.

FIG. 2 depicts the front view of the multi-laser system 100 depicted in FIG. 1. As described above, in some embodiments, the thermally stable enclosure 250 is hermetically sealed. The hermetic sealing may be provided by O-rings 233. Again, hermetically sealing can reduce particles and contamination from outside the enclosure. Moreover, as described above, a hermetic seal may also reduce or prevent the flow of air currents and thus prevent or reduce the flow of ambient temperature changes into the enclosure. This in turn may reduce temperature instability within the enclosure. In some embodiments, the top of enclosure 250 may be thermally coupled, possibly with a copper braid, to the main body of the enclosure 250 to reduce thermal effects.

As shown in FIG. 2, the multi-laser system may further comprise a temperature controller 252. In some embodiments, the temperature controller 252 may comprise a thermo electric cooler (TEC), a temperature sensor and control electronics. The TEC may pump heat from one side to the other depending on the direction of current flow through the TEC. The direction of current flow may be determined by the control electronics. In some embodiments, for example, if the ambient temperature were higher than the enclosure 250's set point temperature then the control electronics may direct current flow through the TEC so that heat was pumped out of the enclosure 250 thereby helping maintain the enclosure's set point temperature. In other embodiments, if the ambient temperature were lower than the enclosure 250's set point temperature, then the control electronics may reverse the current flow through the TEC so that heat was pumped into the enclosure 250 again helping maintain the enclosure's set point temperature. A temperature controller 252 can be thermally coupled to the thermally stable enclosure 250. The temperature controller 252 can include a temperature sensor (not shown) to measure the temperature of the thermally stable enclosure 250, and to provide feedback to the control electronics. In some embodiments, the temperature sensor may comprise a thermistor. The temperature controller 252 may remove heat from or add heat to the thermally stable enclosure 250 in order to maintain a substantially constant temperature in the thermally stable enclosure 250. The high thermal conductivity of the material of the enclosure 250 helps the temperature controller to relatively quickly adjust the temperature within the enclosure 250 in response to temperature variations outside of the enclosure 250 and also reduce the presence of temperature variations across the enclosure 250.

As shown in FIG. 2, the multi-laser system may also comprise a baseplate 260. The baseplate 260 may act as a thermal heat sink for the temperature controller 252.

In some embodiments, the temperature within the thermally stable enclosure 250 can be held stable to within ±1° C., ±2° C., ±3° C., ±5° C., etc., for example, of a target temperature. In some embodiments, the temperatures of the wavelength selective mirrors and the focusing optics can be held to be within ±1° C., ±2° C., ±3° C., ±5° C., etc. of one another. In some embodiments, the temperature over a substantial portion of the enclosure can be held to be within ±1° C., ±2° C., ±3° C., ±5° C., etc. In some embodiments, the temperature over the entire enclosure can be held to be within ±1° C., ±2° C., ±3° C., ±5° C., etc., for example, of a target temperature. In some embodiments, the temperature within the enclosure can be held to be within ±1° C., ±2° C., +3° C., ±5° C., etc., for example, of a target temperature. In some embodiments, the temperature within the thermally stable enclosure 250 can be held within ±1° C. of the target temperature. In some embodiments, the target temperature can be between 10° C. and 50° C. In some embodiments, the target temperature can be between about 15° C. and 45° C. In other embodiments, the target temperature can be between about 15° C. and 35° C. In other embodiments, the target temperature can be between about 10° C. and 40° C. The temperature controller 252 also maintains the focused laser beams aligned with respect to the flow cell over a wide range of ambient temperatures. In some embodiments, the range of ambient temperatures can be between 10° C. and 50° C. In some embodiments, the range of ambient temperatures can be between about 15° C. and 45° C. In other embodiments, the range of ambient temperatures can be between about 15° C. and 35° C. In other embodiments, the range of ambient temperatures can be between about 10° C. and 40° C.

FIG. 2 also depicts that the three lasers 201, 202, and 203 may be placed at different heights within the enclosure 250. The placement at different heights may assist in positioning the focused laser beams at a desired spacing from one another at the flow cell. By disposing the lasers at different heights, the focused beams at the flow cell may be separated by between about 110 µm and 140 µm of one another. The wavelength selective mirrors, however, can additionally be adjusted to account for the imperfection in laser positions that may result, for example, from manufacturing tolerances. Accordingly, the wavelength selective mirrors may establish better positioning of the beams directed onto the flow cell.

Figure 3:
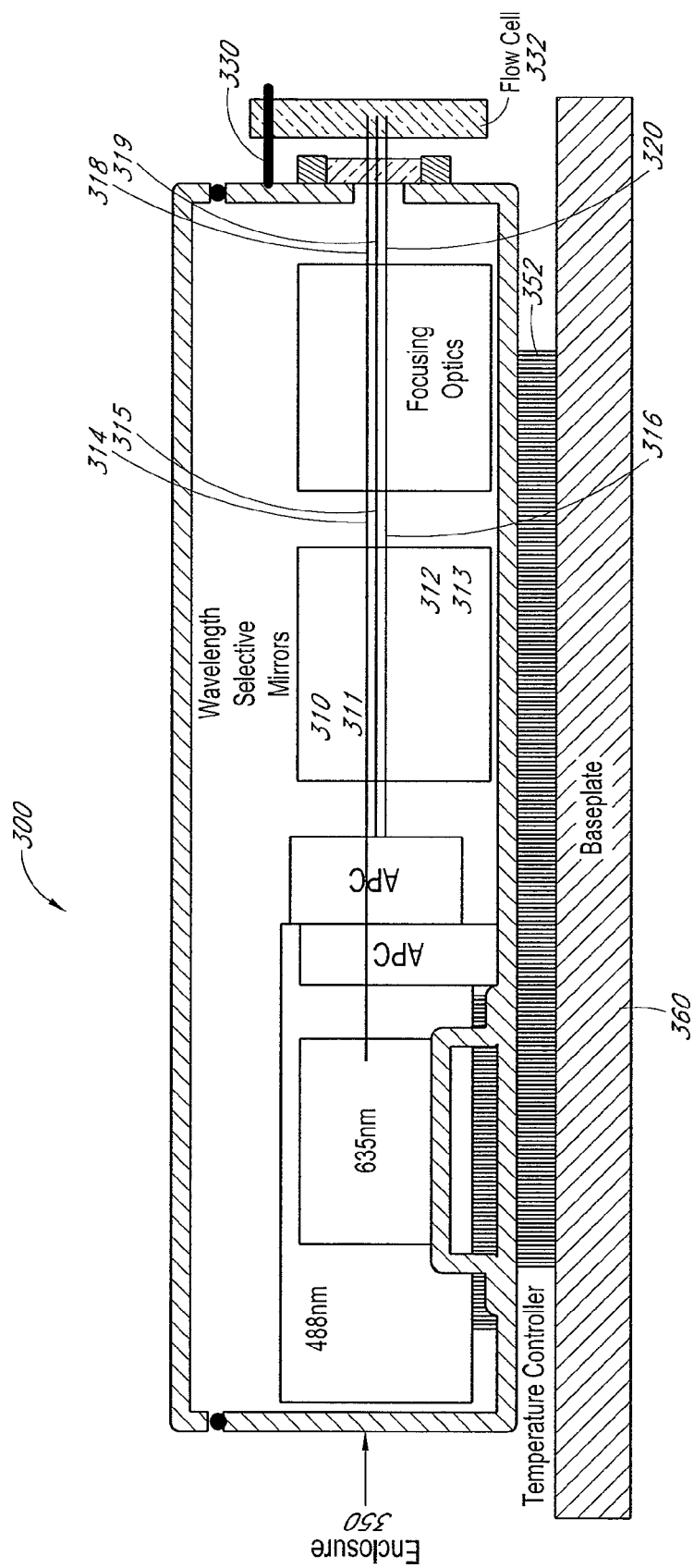
FIG. 3 depicts the side view of the system of FIG. 1.

FIG. 3 depicts the side view of the multi-laser system 100 depicted in FIG. 1. FIG. 3 also shows the placement of the lasers at different heights. The thermally stable enclosure 350 comprises wavelength selective mirrors 310, 311, 312 and 313 that are configured to adjust the position of the plurality of laser beams 314, 315 and 316 to be at a certain distance of one another, in addition to the spacing adjustment that may be provided by placing the lasers at different heights within the enclosure 350. In some embodiments, the laser beams can be positioned to be coaxially, slightly offset but parallel to each other or slightly offset but not parallel to each other. In some embodiments, the plurality of focused laser beams 318, 319 and 320 may be separated by about 110 µm and 140 µm of one another. In some embodiments, the plurality of focused laser beams 318, 319 and 320 may be positioned to be at a distance of about 125 µm of one another.

As can be seen in FIG. 3, the thermally stable enclosure 350 comprises a top, a bottom, and four sides. In some embodiments, the thermally stable enclosure 350 has a width of about 3 inches or less, a length of about 6 inches or less, and a height of about 2 inches or less. In other embodiments, the length, the width and the height of the thermally stable enclosure 350 may be relatively larger or smaller. In some embodiments, the thermally stable enclosure 350 has a volume of 36 cubic inches or less. With a relatively small volume, the temperature controller is better able to adjust the temperature of the enclosure and system in response to variations in ambient temperature. The temperature controller is thus able to avoid temporal variations in temperature induced by fluctuation in ambient conditions. Similarly the relatively small volume may reduce temperature instabilities within the enclosure 350 by reducing temperature gradients across the enclosure 350. In other embodiments, the volume of the thermally stable enclosure 350 may be relatively larger or smaller. Also shown in FIG. 3 is the flow cell connection 330, described above.

Reference throughout this specification to "some embodiments," "certain embodiments," or "an embodiment" means that a particular feature, structure or characteristic described in connection with the embodiment is included in at least some embodiments. Thus, appearances of the phrases "in some embodiments" or "in an embodiment" in various places throughout this specification are not necessarily all referring to the same embodiment and may refer to one or more of the same or different embodiments. Furthermore, the particular features, structures or characteristics may be combined in any suitable manner, as would be apparent to one of ordinary skill in the art from this disclosure, in one or more embodiments.

As used in this application, the terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Similarly, it should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Rather, inventive aspects lie in a combination of fewer than all features of any single foregoing disclosed embodiment.

Although the inventions presented herein have been disclosed in the context of certain preferred embodiments and examples, it will be understood by those skilled in the art that the inventions extend beyond the specifically disclosed embodiments to other alternative embodiments and/or uses of the inventions and obvious modifications and equivalents thereof. Thus, it is intended that the scope of the inventions herein disclosed should not be limited by the particular embodiments described above.

What is claimed is:

1. A compact, thermally stable multi-laser system, comprising:

a plurality of lasers outputting a plurality of respective laser beams;

a beam positioning system configured to position the plurality of laser beams closer together;

beam focusing optics configured to focus the plurality of laser beams;

a thermally stable enclosure enclosing the plurality of lasers, the beam positioning system, and the beam focusing optics, and configured to thermally and mechanically couple to a flow cell, said thermally stable enclosure substantially comprising a material with high thermal conductivity of at least 5 W/(m K), and having a volume of 36 cubic inches or less; and a temperature controller configured to control a temperature of said enclosure and flow cell and to align the focused laser beams to the flow cell over a range of ambient temperatures.

2. The system of claim 1, wherein the plurality of lasers comprises at least one diode laser.

3. The system of claim 1, wherein the plurality of lasers comprises at least one solid-state laser.

4. The system of claim 1, wherein the plurality of lasers comprises at least one frequency-doubled laser.

5. The system of claim 1, wherein the plurality of laser beams comprises at least a first laser beam at a first wavelength, a second laser beam at a second wavelength, and a third laser beam at a third wavelength, said first, second and third wavelengths being different from one another.

6. The system of claim 1, wherein the beam positioning system comprises a plurality of dichroic and trichroic mirrors.

7. The system of claim 6, further comprising a plurality of flexure mounts supporting the plurality of dichroic and trichroic mirrors.

8. The system of claim 6, wherein the dichroic and trichroic mirrors are configured with highly reflective and anti-reflective coatings in accordance with the respective wavelength of the plurality of laser beams.

9. The system of claim 6, wherein the dichroic and trichroic mirrors are configured to position at least two of the plurality of laser beams substantially coaxially, offset but parallel to each other or offset but not parallel to each other.

10. The system of claim 9, wherein the focused laser beams have centers separated by between about 110 μm and 140 μm of one another at the flow cell.

11. The system of claim 1, further comprising an automatic power control module for each laser of said plurality of lasers.

12. The system of claim 11, wherein the automatic power control module comprises a beam splitter and photodetector configured to sample light from the laser beam of each laser and to provide feedback to a laser controller to adjust each laser output power.

13. The system of claim 1, wherein the beam focusing optics includes an achromatic and anamorphic lens system to provide an output laser beam with an elliptical shape.

14. The system of claim 1, wherein the beam focusing optics includes an achromatic cylindrical lens to provide an output laser beam with an elliptical shape.

15. The system of claim 1, wherein the beam focusing optics includes an achromatic spherical lens to provide an output laser beam with an elliptical shape.

16. The system of claim 1 further comprising polarization rotators or waveplates which may be used to rotate the laser beam polarization to obtain a laser beam polarization orientation with respect to the laser beam geometry that enhances system performance.

17. The system of claim 1, wherein the beam focusing optics includes an anamorphic prism system to provide an output laser beam with an elliptical shape.

18. The system of claim 1, wherein the focused laser beams have respective spot sizes of between about 70 μm and 110 μm in one direction.

19. The system of claim 1, wherein the focused laser beams have respective spot sizes of between 6 μm and 14 μm in one direction.

20. The system of claim 1, wherein the material with high thermal conductivity comprises copper.

21. The system of claim 1, wherein the material with high thermal conductivity comprises copper tungsten material.

22. The system of claim 1, wherein the material with high thermal conductivity comprises aluminum material.

23. The system of claim 1, wherein the thermally stable enclosure comprises a top, a bottom and four sides.

24. The system of claim 1, wherein the thermally stable enclosure maintains a temporal temperature variation of less than about 1° C. within the enclosure.

25. The system of claim 1, wherein the thermally stable enclosure has a width of about 3 inches or less.

26. The system of claim 1, wherein the thermally stable enclosure has a length of about 6 inches or less.

27. The system of claim 1, wherein the thermally stable enclosure has a height of about 2 inches or less.

28. The system of claim 1, wherein the thermally stable enclosure is hermetically sealed.

29. The system of claim 1, wherein the thermally stable enclosure matches the thermal expansion coefficient of the flow cell.

30. The system of claim 1, wherein the temperature controller comprises a thermal electric cooler, a temperature sensor and control electronics.

31. The system of claim 1, wherein the range of ambient temperatures is between about 10° C. and 40° C.

32. The system of claim 1, wherein the relative heights of the lasers in the enclosure assists in the relative positioning of the focused laser beams at the flow cell.

33. The system of claim 1, wherein the focused laser beams have centers separated by between about 110 μm and 140 μm of one another at the flow cell.

* * * * *